US00PP20146P2

(12) United States Plant Patent
van der Spek

(10) Patent No.: US PP20,146 P2
(45) Date of Patent: Jun. 30, 2009

(54) ***HYDRANGEA* PLANT NAMED 'SIDASAB'**

(50) Latin Name: *Hydrangea macrophylla*
Varietal Denomination: Sidasab

(76) Inventor: Daniel van der Spek, Nieuwkoopseweg 45, 2631 PP Nootdorp (NL)

( * ) Notice: Subject to any disclaimer, the term of this patent is extended or adjusted under 35 U.S.C. 154(b) by 0 days.

(21) Appl. No.: 11/903,266

(22) Filed: Sep. 22, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette H Para
*Assistant Examiner*—Louanne C Krawczewicz Myers

(57) ABSTRACT

A new and distinct *Hydrangea* cultivar named 'Sidasab' is disclosed, characterized by white flowers with pink margins, slow to moderate growth habit and a compact inflorescence. The new variety is a *Hydrangea,* and naturally blooms from April through September.

1 Drawing Sheet

Latin name of the genus and species: *Hydrangea macrophylla.*
Variety denomination: 'Sidasab'.

BACKGROUND OF THE INVENTION

The new cultivar is a product of a planned breeding program. The intent of this breeder program was stronger pot plant varieties with attractive flower colors. The new variety was discovered as seedling within the planned breeding program. This seedling is a result from the crossing of the female parent, an undistributed proprietary variety referred to as 9825 with the male parent, an undistributed proprietary variety referred to as 9659. 'Sidasab' was selected as a single plant by Daniel van der Spek in May of 2002 in Nootdorp, the Netherlands.

Asexual reproduction of the new cultivar 'Sidasab' by vegetative cuttings was performed in Nootdorp, the Netherlands and has shown that the unique features of this cultivar are stable and reproduced true to type on successive generations.

SUMMARY OF THE INVENTION

The cultivar 'Sidasab' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Sidasab' These characteristics in combination distinguish 'Sidasab' as a new and distinct *Hydrangea* cultivar:

1. Mop-head inflorescence;
2. Unique petal coloration of white with pink margins;
3. dark foliage;
4. Strong plant, resisting breaking in production and post-harvest situations.

Plants of the new cultivar 'Sidasab' are similar to plants of the female parent, '9825,' in most horticultural characteristics, however, plants of the new cultivar 'Sidasab' has significantly different flower coloration. Flowers of the new cultivar are white with red margins, while the female parent has simply white flower coloration. 'Sidasab' differs from the male parent '9659' in foliage color. Foliage of the new cultivar is 139B, much darker than the male parent. Additionally, the new variety has smaller leaves as well as more leaves per lateral branch.

Plants of the new cultivar 'Sidasab' are similar to plants of the commercial variety 'Sandra' undistributed and unpatented in the United States, in plant shape and having a two-color flower. However, plants of the new cultivar 'Sidasab' differ in the following characteristics;

1. Infloresence type of 'Sidasab' is mop-head whereas 'Sandra' is lace-cap
2. Pink petal margins are wider in the new cultivar 'Sidasab'
3. Calyx shape of 'Sidasab' is inconspicuous, while calyx shape of 'Sandra' is conspicuous.

BRIEF DESCRIPTION OF THE PHOTOGRAPH

The accompanying photograph in FIG. 1 illustrates in full color a typical blooming plant of 'Sidasab' grown in a greenhouse. The photograph was taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart except where general terms of ordinary dictionary significance are used. The following observations and measurements describe 'Sidasab' plants grown in a greenhouse in Brielle, The Netherlands from October 2005 to October 2006. The growing temperature ranged from 16° C. to 17° C. at night to 18° C. to 20° C. during the day. The pH of the growing medium was between 5.0 and 5.5. Measurements and numerical values represent averages of typical flowering types.

Botanical classification: *Hydrangea macrophylla* cultivar 'Sidasab.'

PROPAGATION

Time to rooting: 19 to 21 days at approximately 20° C.
Root description: Fine, fibrous.

PLANT

Growth habit: Flowering perennial shrub.
Height: Approximately 36 cm from soil level to the top of the inflorescence.
Blooming period: April through September.
Plant spread: Approximately 53.5 cm.
Growth rate: Moderate.
Branching characteristics: Moderately free branching.
Length of lateral branches: Approximately 22 cm.
Number of lateral Branches: Approximately 11.
Diameter of lateral Branches: Approximately 0.5 cm.
Pinching required: Yes.
*Details of pinching.*—The first pinch is given at 8 weeks from the planting of a rooted cutting. A second pinch is given 12 weeks from planting a rooted cutting.
Lateral branch shape: Round.
Lateral branch strength: Very strong.
Lateral branch texture: Leathery.
Lateral branch color: Approximately RHS Yellow-Green 144B, slightly tinged at the nodes with RHS Greyed-Purple 187D.
Other stem or plant characteristics: Stems covered with lenticels at a density of approximately 4.5 lenticels per square cm.
*Lenticel length.*—Approximately 1.5 mm.
*Lenticel width.*—Approximately 0.75 mm.
*Lenticel color.*—About RHS Greyed-Purple 187D.
Number of leaves per lateral branch: Approximately 8.
Age of plant described: Approximately 1 year.

FOLIAGE

Leaf:
*Arrangement.*—Opposite.
*Compound or single.*—Single
*Average length.*—Approximately 11.8 cm.
*Average width.*—Approximately 7.5 cm.
*Shape of blade.*—Broad oval to broad elliptic oblong.
*Apex.*—Apiculate
*Base.*—Obtuse.
*Attachment.*—Stalked.
*Margin.*—Serrate, approximately 2 teeth per cm.
*Texture of top surface.*—Glossy, non-pubescent.
*Texture of bottom surface.*—Matte, non-pubescent.
*Leaf internode length.*—Approximately 6.1 cm.
*Color.*—Young foliage upper side. Near R.H.S. Green 137A. Young foliage underside: Near R.H.S. Yellow-Green 146B. Mature foliage upper side: Near R.H.S. Green 139B. Mature foliage under side: Near R.H.S. Green 138B.
*Venation.*—Type: Pinnate Venation color upper side: Near R.H.S. Yellow-Green 145C. Venation color under side: Near R.H.S. Yellow-Green 145B.
*Durability of foliage to stresses.*—High.
Petiole:
*Average length.*—Approximately 2.2 cm.
*Color.*—Near R.H.S. Yellow-Green 145B.
*Diameter.*—Approximately 0.3 cm.

FLOWER

Bloom period: Continuous April through September.
Inflorescence:
*Arrangement.*—Terminal inflorescence.
*Type.*—Compound corymb.
*Height.*—Approximately 11.8 cm.
*Width.*—Approximately 16.0 cm.
*Quantity of flowers per inflorescence.*—Fertile flowers, approximately 40. Sterile Flowers, approximately 320.
Bud:
*Bud shape* (*sterile flowers*).—Obovate.
*Bud length* (*sterile flowers*).—Approximately 0.5 cm.
*Bud diameter* (*sterile flowers*).—Approximately 0.3 cm.
*Bud color* (*sterile flowers*).—Near R.H.S. Greyed-Purple 186D. Top: Near R.H.S. Greyed-Purple 186C Base/calyx. Near R.H.S. 147C.
*Bud shape* (*fertile flowers*).—Globose.
*Bud length* (*fertile flowers*).—Approximately 0.7 cm.
*Bud diameter* (*fertile flowers*).—Approximately 0.7 cm.
*Bud color* (*fertile flowers*).—Near RHS Orange-White 159C. Fertile flowers do not open.
Flower:
*Shape.*—Rotate.
*Facing direction.*—All directions.
*Quantity of flowers per lateral stem.*—360.
*Quantity of flowers and buds per plant.*—Approximately 3600.
*Diameter of entire flower.*—Fertile; Approximately 0.7 cm. Sterile: Approximately 4.0 cm.
*Depth of flower.*—Fertile; Approximately 0.5 cm. Sterile: Approximately 1.2 cm.
*Rate of opening.*—Individual flowers: Fully open approximately 5 days from the bud stage. Whole Plant: Approximately 50% of flowers open at once.
*Flower longevity on plant.*—Fertile flowers: Approximately 5 days. Sterile flowers: Approximately 25 days.
*Persistent or self-cleaning.*—Persistent.
*Fragrance.*—No.
Petals:
*Length of petal.*—Approximately 0.4 cm.
*Width of petal.*—Approximately 0.25 cm.
*Shape of petal.*—Ovate.
*Apex shape of petal.*—Acute.
*Petal base.*—Cordate.
*Petal margin.*—Entire.
*Petal arrangement.*—Rotate.
*Petal number.*—Approximately 4.
*Petals fused.*—No.
*Petal Appearance.*—Dull.
*Petal texture* (*both surfaces*).—Smooth.
Color:
*Upper surface at first opening.*—Top edge: Near Red-Purple 67B. Base: White 155 with Near Red-Purple 69D.
*Upper surface at maturity.*—Top edge: Near Red-Purple 67B. Base: White 155 with Near Red-Purple 69D.
*Upper surface at fading.*—Top edge: Near Red-Purple 67B. Base: White 155 with Near Red-Purple 69D.
*Under surface at first opening.*—Near Red-Purple 67B.

*Under surface at maturity.*—Top edge: Near Red-Purple 67B. Base: White 155 with Near Red-Purple 69D.

*Under surface at fading.*—Top edge: Near Red-Purple 67B. Base: White 155 with Near Red-Purple 69D.

Petaloids: No.

Fragrance: None.

CALYX

Present: Yes.

Shape: Rotate, lower ⅔ fused.

Length: Approximately 0.3 cm.

Diameter: Approximately 1.4 cm.

SEPAL

Sepals: Only sterile flowers have sepals. Fertile flowers do not open.

Number: 5

Sepal texture (both surfaces): Smooth.

Sepal arrangement: Rotate.

Sepal shape: Deltoid.

Sepal length: Approximately 0.3 cm.

Sepal width: Approximately 0.1 cm.

Apex shape: Acute.

Base: Fused into a tube ⅔ of length.

Margin: Entire.

Color: Upper side near R.H.S. Green 143D. Under side near R.H.S. Green 143D.

PEDUNCLE

Length: Approximately 6.8 cm.

Diameter: Approximately 0.35 cm

Angle: Approximately 25 degrees (0 degrees=straight upright)

Strength: Strong

Color: Near R.H.S. Yellow-Green 144B

PEDICEL

Present: Yes.

Length (sterile flowers): Approximately 2.0 cm.

Diameter (sterile flowers): Approximately 1.5 cm.

Angle (sterile flowers): Approximately 5 degrees.

Strength (sterile flowers): Moderate

Color (sterile flowers): Near White 155A, slightly tinged base near R.H.S. Greyed-Purple 187D.

Length (fertile flowers): Approximately 0.7 cm.

Diameter (fertile flowers): Approximately 0.3 cm.

Angle (fertile flowers): Approximately 10 degrees.

Strength (fertile flowers): Moderate

Color (fertile flowers): Near Orange-White 159D.

REPRODUCTIVE ORGANS

*Number of pistils per flower.*—3.

*Pistil length.*—Approximately 0.15 cm.

*Stigma shape.*—Lobed.

*Stigma color.*—Near Red-Purple 57D.

*Style color.*—Near Red-Purple 62D.

*Style length.*—Approximately 0.05 cm.

*Ovary color.*—Near Yellow-Green 154D.

*Stamens.*—Average 8.

*Anther shape.*—Broad kidney-shaped.

*Anther color.*—Near Greyed-White 156D, filament colored Red-Purple 62C.

*Pollen color.*—Near White 155A.

*Pollen Quantity.*—Very low.

OTHER CHARACTERISTICS

Disease resistance: Neither resistance nor susceptibility to diseases or pests has been observed in this variety.

Drought tolerance and cold tolerance: Semi-hardy perennial, tolerant of some high temperatures. Upper limit of temperature tolerance has not been observed, however, known to tolerate temperatures of at least up to 40° C. Lower limits have also not been observed, however, observed hardy to −15° C. No drought tolerance has been observed.

Fruit/Seed production: No fruits/seeds detected to date.

What is claimed is:

1. A new and distinct cultivar of *Hydrangea* plant named 'Sidasab' as herein illustrated and described.

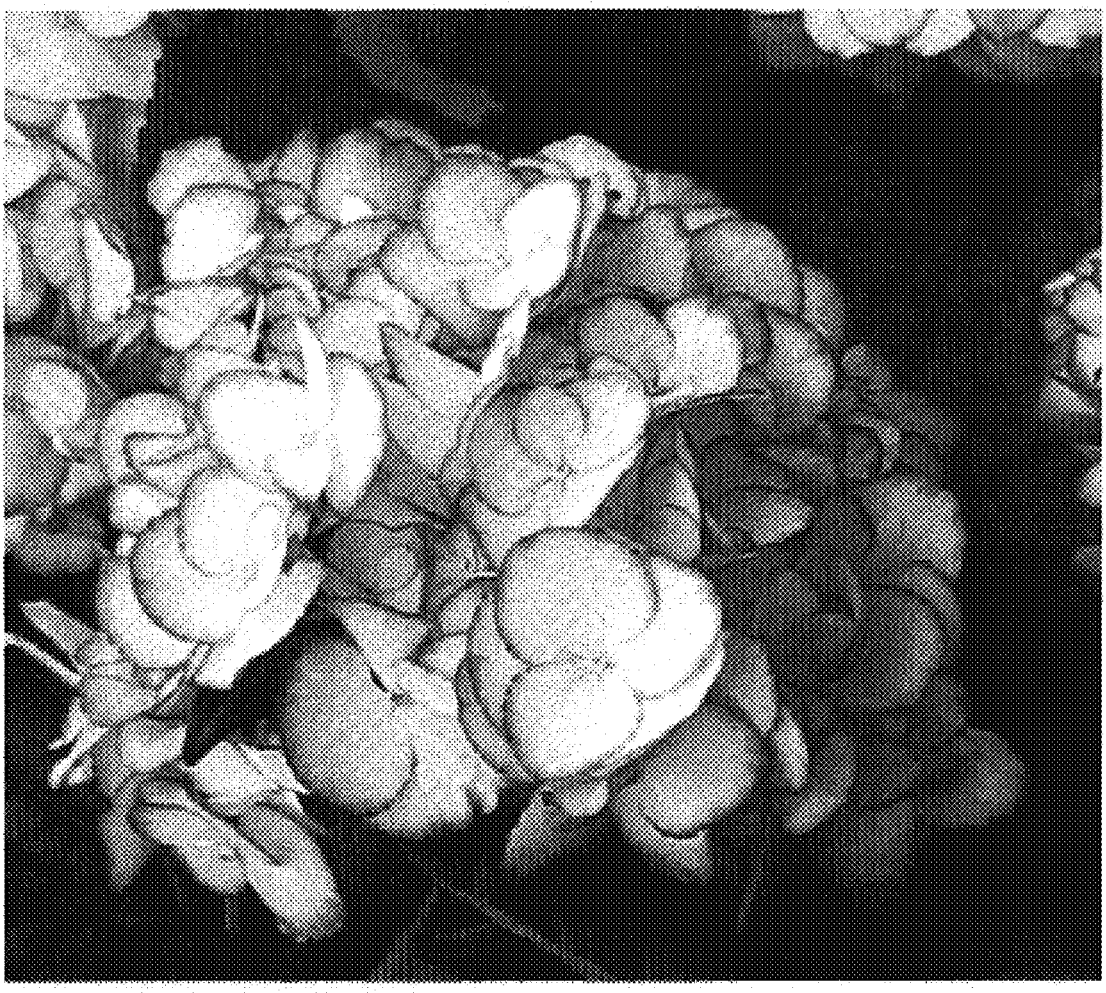

* * * * *